United States Patent [19]

Gonzalez

[11] 4,418,056

[45] Nov. 29, 1983

[54] PROCESS FOR MAKING CUPRIC HYDROXIDE

[75] Inventor: Mario R. R. Gonzalez, Colonia Industrial Vallejo La Patera, Mexico

[73] Assignee: Cuproquim S.A., Mexico City, Mexico

[21] Appl. No.: 453,212

[22] Filed: Dec. 27, 1982

[51] Int. Cl.$^3$ .................... C01G 3/02; A01N 59/20; A61K 33/34

[52] U.S. Cl. .................... 424/142; 413/265; 413/604

[58] Field of Search .................. 423/27, 35, 604, 265; 424/140, 142

[56] References Cited

U.S. PATENT DOCUMENTS

| | | | |
|---|---|---|---|
| 1,920,053 | 7/1933 | Bassett | 423/265 |
| 2,089,612 | 8/1937 | Kubelka | 424/142 |
| 2,551,446 | 5/1951 | Marks | 424/142 |
| 3,287,209 | 11/1966 | Simmons | 424/142 |
| 3,428,731 | 2/1969 | Furness | 424/140 |
| 4,097,271 | 6/1978 | Swinkels | 423/604 |
| 4,292,281 | 9/1981 | Chilcote | 423/604 |

*Primary Examiner*—Brian E. Hearn
*Attorney, Agent, or Firm*—Darryl M. Springs

[57] ABSTRACT

In one exemplar embodiment, the present invention comprises a method of making cupric hydroxide that comprises the steps of preparing a suspension of insoluble copper oxychloride in aqueous medium, mixing sodium lignosulfonate into the copper oxychloride suspension for more uniformly dispersing the copper oxychloride particles in the aqueous medium agitating the copper oxychloride suspension and added sodium lignosulfonate until a desired viscosity is obtained, adding sodium hydroxide to the copper oxychloride suspension for reacting with the copper oxychloride to form cupric hydroxide, and recovering the cupric hydroxide.

4 Claims, No Drawings

PROCESS FOR MAKING CUPRIC HYDROXIDE

BACKGROUND OF THE INVENTION

This invention relates to a process for making a stable copper (cupric) hydroxide by means of reacting sodium hydroxide with copper oxychloride.

DESCRIPTION OF THE PRIOR ART

There are numerous ways disclosed in the prior art for making cupric hydroxide. One technique uses a copper sulfate solution reacted with ammonia to form cupric hydroxide and a compound containing the sulfate radical for particular use in the preparation of a cuprammonium cellulose solution in making rayon as disclosed in U.S. Pat. No. 2,758,013. Others disclose use of a copper sulfate solution reacted with ammonia and then with an alkali metal hydroxide (such as sodium hydroxide) to precipitate non-soluble cupric hydroxide as shown in U.S. Pat. Nos. 1,800,828; and 1,867,357. Another variation of the ammonia reaction processes is the reaction under anhydrous conditions of an inorganic copper salt, ammonia and a lower alkanol solvent for the inorganic copper salt to form a resulting complex which is then reacted with an alkali metal hydroxide, with the resulting complex decomposed under vacuum to obtain cupric hydroxide as disclosed in U.S. Pat. No. 3,956,475. It is known that stable, separable cupric hydroxide cannot generally be made by direct reaction between copper sulphate and sodium hydroxide. The combination of these two chemicals results in the formation of blue cupric hydroxide in a sludge form but which rapidly decomposes to black cupric oxide. U.S. Pat. No. 1,920,053 discloses a process for making cupric hydroxide from copper sulfate and excess sodium hydroxide carried out at low temperatures (below 10° C.) to help overcome this problem. Another process for making cupric hydroxide is disclosed in U.S. Pat. No. Re. 24,324 in which trisodium phosphate is reacted with copper sulfate to form copper sodium phosphate which is in turn reacted with sodium hydroxide to precipitate cupric hydroxide.

All of the prior art processes are too complex or expensive or fail to produce a stable form of cupric hydroxide suitable for large scale production, particularly for use as an agricultural fungicide and bactericide.

SUMMARY OF THE INVENTION

The present invention remedies the problems of the prior art by providing a process or method of making cupric hydroxide that comprises the steps of preparing a suspension of insoluble copper oxychloride in an aqueous medium, mixing sodium lignosulfonate into the copper oxychloride suspension for more uniformly dispersing the copper oxychloride particles in the aqueous medium, agitating the copper oxychloride suspension and added sodium lignosulfonate until a desired viscosity is reached, adding sodium hydroxide to the copper oxychloride suspension for reacting with the copper oxychloride to precipitate cupric hydroxide, the sodium lignosulfonate further acting to stabilize the cupric hydroxide formed, and recovering the cupric hydroxide. The cupric hydroxide made according to this process is extremely stable, is the result of a one-reaction process, and enables a manufacturer to produce cupric hydroxide in large bulk quantities at lower prices than presently possible.

BRIEF DESCRIPTION OF THE PREFERRED EMBODIMENTS

The present process for making stable cupric hydroxide, which is particularly suited for large scale production in manufacturing agricultural fungicides and bactericides, includes the following basic steps:

Step 1—Prepare a suspension of insoluble copper oxychloride ($CuCl_2.3Cu(OH)_2$) in an aqueous medium of any convenient concentration and place in a suitable mixing vessel;

Step 2—Add sodium lignosulfonate (approximately 1% by weight) to the copper oxychloride suspension and agitate until the mixture achieves a desired viscosity as judged by when it takes on a "smooth" or "creamy" appearance as judged by eye;

Step 3—As rapidly as possible, add a sodium hydroxide solution (NaOH) of 50.0% concentration and containing an excess quantity of sodium hydroxide then stoichiometrically necessary to react with the copper oxychloride to form cupric hydroxide to the mixture of sodium lignosulfonate and copper oxychloride suspension and continue agitation until the resulting reaction slurry (comprising a suspension of cupric hydroxide in the resultant reaction) changes color from light blue or gray-blue to a dark blue (as judged by eye and memory);

Step 4—Stop agitation and collect the cupric hydroxide ($Cu(OH)_2$) from the slurry by vacuum filtration. The above process is carried out at normal room temperatures.

The collected cupric hydroxide filter cake is washed with fresh water until the pH is lowered to approximately 8. The washed dark blue filter cake may then be dried in any convenient manner to obtain a dried granular form of cupric hydroxice. The resultant aqueous filtrate or mother liquor, primarily a sodium chloride colution (NaCl) with remaining sodium lognosulfonate, is disposed of as waste.

In preparing large quantities of cupric hydroxide in the batch process, it has been found that certain preferred quantities and concentrations of starting materials yield the best results. For example, if it is desired for the above process to yield one ton of cupric hydroxide, then the copper oxychloride suspension in an aqueous medium should preferably be 9120 liters and have a concentration of 98 grams per liter. The pH range desired is 6–7. The quantity of sodium lignosulfonate added would be 11 kilograms. The sodium hydroxide solution should be a 50% concentration containing a maxium of 410 kilograms of the sodium hydroxide dry base. While varying percentages of excess sodium hydroxide than that necessary to stoichiometrically react with the copper oxychloride to form cupric hydroxide may be used, it has been found that large excess percentages, for example 80.0%, are preferable to accelerate the reaction rate and form the desired size of cupric hydroxide particles of crystals in suspension.

The sodium lignosulfonate is a metallic sulfonate salt made from the lignin of sulfite pulp-mill liquors and has molecular weights ranging from 1,000 to 20,000. The lignosulfonate does not chemically react with copper oxychloride or sodium hydroxide, but is added to the copper oxychloride suspension to act as a dispersing agent to more uniformly disperse the suspended insoluble copper oxychloride particles in the aqueous medium for enhancing the resultant chemical reaction of the copper oxychloride and sodium hydroxide. It is also believed that tht sodium lignosulfonate acts as a stabilizer of the resultant cupric hydroxide formed and prevents its decomposition to useless cupric oxide by preventing water loss from the cupric hydroxide.

There is no exact formula for the starting material copper oxychloride, but it has been found convenient to use the following formulation:

$CuCl_2 \cdot 3Cu(OH)_2$ which when reacted with the sodium hydroxide provides:

$CuCl_2 \cdot 3Cu(OH)_2 + 2NaOH \rightarrow 4Cu(OH)_2 + 2NaCl$ of course, other convenient copper oxychloride formulas may be used. In the process Step 3 above described in making the large quantity (one ton) of cupric hydroxide, the time period for agitation of the combined sodium hydroxide solution and copper oxychloride suspension and sodium lignosulfonate to effect the desired "dark blue" color is approximately 20 minutes.

The dried granular cupric hydroxide is formulated for final use as an agricultural fungicide or bactericide by mixing with sodium lignosulfonate (7.0% by weight), a suitable wetting agent (such as nonyl phenol exhoxilate or other suitable agent) (less than 1.0% by weight) and calcium carbonate (about 16% by weight). The calcium carbonate is used as a filler to reduce the copper concentration in the final product to a maximum of 50%. The above mixture is then pulverized in a hammer mill to a fine powder to form the final stable cupric hydroxide product.

What is claimed is:

1. A method for making a stable cupric hydroxide which comprises the steps of:

preparing a suspension of insoluble copper oxychloride in an aqueous medium, adding sodium lignosulfonate to said aqueous suspension of copper oxychloride for more uniformaly dispersing said copper oxychloride in suspension, agitating the copper oxychloride suspension and added sodium lignosulfonate until a desired viscosity is reached, continuing agitation of the mixture of sodium lignosulfonate and the copper oxychloride suspension while rapidly adding a sodium hydroxide solution to react with said copper oxychloride to form cupric hydroxide, said sodium lignosulfonate further acting as a stabilizer to prevent water loss from the cupric hydroxide, and recovering the cupric hydroxide.

2. A method for making a stable cupric hydroxide which comprises the steps of:

preparing a suspension of insoluble copper oxychloride in an aqueous medium, the concentration of said copper oxychloride being 98 grams per liter, adding approximately 1.0% by weight sodium lignosulfonate to said copper oxychloride suspension for more uniformly dispersing said copper oxychloride in suspension, agitating the copper oxychloride suspension and added sodium lignosulfonate until a desired viscosity is reached, continuing agitation of the mixture of sodium lignosulfonate and copper oxychloride suspension while rapidly adding a 50.0% concentration of a sodium hydroxide solution that contains up to an 80% excess of sodium hydroxide by weight over the stoichiometrically equivalent quantity necessary to react with said copper oxychloride to form cupric hydroxide, said sodium lignosulfonate further acting as a stabilizer to prevent water loss from the cupric hydroxide, and recovering the cupric hydroxide.

3. The method as described in claims 1 or 2 above, further including the step of drying said recovered cupric hydroxide to a granular form.

4. The method as described in claim 3, wherein said dried granular cupric hydroxide is further mixed with sodium lignosulfonate, a wetting agent and an inert filler material and pulverized to a finely powdered cupric hydroxide product having a maximum final copper concentration of 50.0%.

* * * * *